United States Patent [19]

Smith

[11] 4,193,694
[45] Mar. 18, 1980

[54] PHOTOSENSITIVE COLOR MONITORING DEVICE AND METHOD OF MEASUREMENT OF CONCENTRATION OF A COLORED COMPONENT IN A FLUID

[76] Inventor: Charles R. Smith, 421 Westminster, Wenonah, N.J. 08090

[21] Appl. No.: 921,746

[22] Filed: Jul. 3, 1978

[51] Int. Cl.$^2$ .................. G01N 21/04; G01J 21/02
[52] U.S. Cl. ................................ 356/407; 356/411; 356/414; 356/419; 356/425
[58] Field of Search .............. 356/320, 407, 410, 411, 356/414, 419, 425

[56] References Cited

U.S. PATENT DOCUMENTS 3,992,110  11/1976  Frazer et al. .................. 356/419

FOREIGN PATENT DOCUMENTS 1439793  7/1966  France ..................... 356/414

Primary Examiner—Vincent P. McGraw
Attorney, Agent, or Firm—Mortenson & Uebler

[57] ABSTRACT

A color monitoring device is provided for measuring the concentration of a colored component in a flowing gas or liquid stream in which polychromatic light is passed through a frosted lens, then through a transparent sight tube through which the flowing stream passes, then through a second frosted lens, then through a sight mask which divides the light into two beams, one beam then passing through a first filter and the second beam passing through a second filter, the light beams passing through the filters then being directed to a first and second photoconductor, respectively. The first filter is one which absorbs light which is absorbed by the colored component to be measured and passes all other light. The second filter is one which passes light absorbed by the colored component and absorbs light of substantially all other wave lengths. The photoconductors are connected as resistance units in a null circuit such that, when the color component to be measured enters the flowing stream, the light intensity of the beam passing through the first filter is unchanged while the light intensity passing through the second filter is decreased due to the light absorbance by the colored component, this difference in intensity causing an imbalance in the null circuit which can be measured and used to monitor the concentration of the colored component.

4 Claims, 4 Drawing Figures

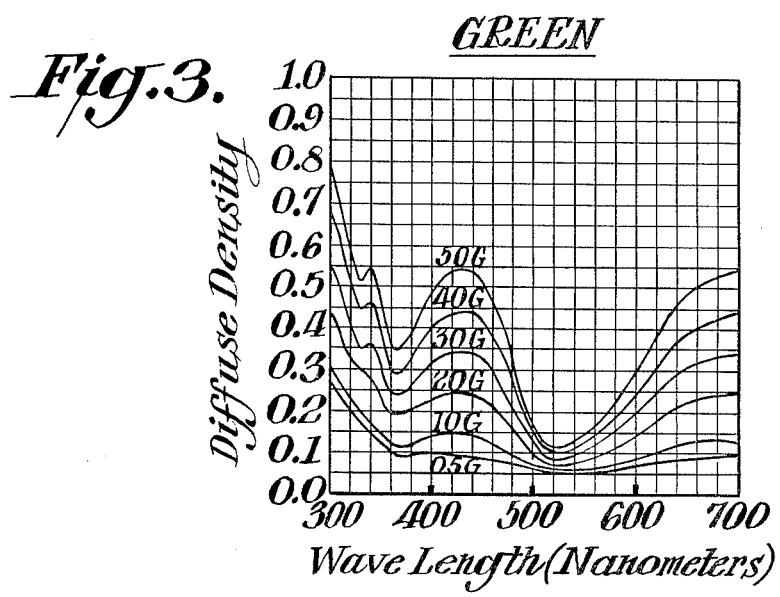
Fig. 3. GREEN
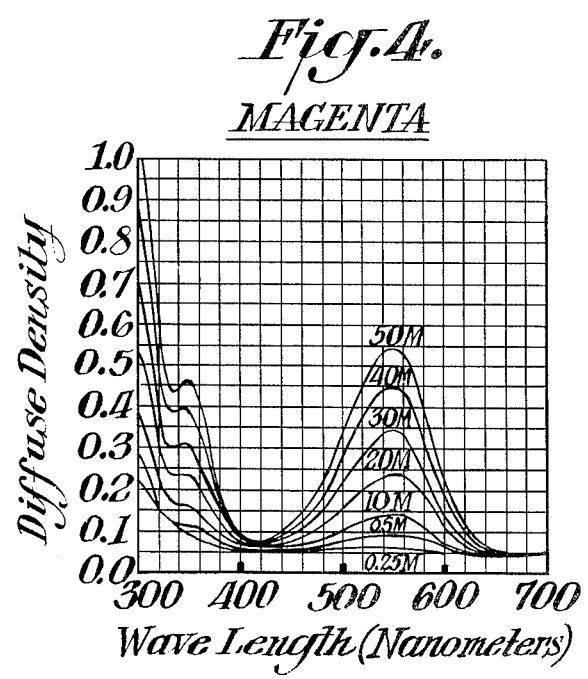
Fig. 4. MAGENTA

PHOTOSENSITIVE COLOR MONITORING DEVICE AND METHOD OF MEASUREMENT OF CONCENTRATION OF A COLORED COMPONENT IN A FLUID

BACKGROUND OF THE INVENTION

This invention concerns a device and method for measuring and continuously monitoring the concentration of a colored component contained in a flowing liquid or gas stream.

Potassium permanganate is often used in water purification systems in quite small concentrations, and it is desirable in such systems to continuously monitor the permanganate concentration.

In refinery products such as gasoline, color concentration is often a specification to be met by the final product, and the quality of final product can often be monitored by measuring the color of intermediates or final product.

This invention is especially suited to the above applications and to other applications in which it is desired to continuously measure the concentration of one or more colored components in a flowing stream containing such components.

Many types of colorimetric devices have been devised in the past to measure the light transmission characteristics of solid, liquid and gaseous materials over wide ranges of light transmission value and wave length. The light absorption of a colored component in a stream varies with the concentration of that component in the stream according to known physical laws. One method for measuring concentration of a colored substance is to measure the light absorbance of the solution by passing light through a predetermined thickness of the solution. Such method is generally unsuitable for streams containing impurities which can affect both the absorbance characteristics of the sample and the intensity of the light passing through the sample.

Dual beam colorimetric devices are also known, in which one beam is passed through the sample to be measured and the second beam is passed through a reference sample of known concentration. Comparison of the output beams from both samples may be detected by photoconductor devices used as resistance elements in a null circuit, and the difference in output of the photoconductors due to a difference in concentration of colored component in the stream to be measured and the reference sample may be detected and monitored by measuring the degree of imbalance of the null circuit. In these dual beam devices, impurities in the stream to be measured other than the component to be measured can cause loss of sensitivity and erroneous readings.

All known prior art colorimetric devices employ optical quality lenses to direct the light beam(s) through the sample to be monitored. Here, also, impurities cause erroneous readings in either single or dual beam devices since an impurity particle will cast a shadow upon the receiving photoconductor causing a decrease in intensity of light reaching that photoconductor which is totally unrelated to the absorbance of light by the colored component of interest.

Specific colorimetric devices which were found during a search of prior art related to this invention include those disclosed in the following patents.

U.S. Pat. No. 3,062,963 (Douty) discloses a method of monitoring colored fluids in which light absorbance of a sample is measured at a wave length of light which is materially absorbed by both the key colored substance to be measured and by the impurities in the stream, and also at a wave length of light which is absorbed by only the impurities. A comparison of the two absorbances provides a measure of the concentration in the stream of a key colored substance.

U.S. Pat. No. 2,895,055 (Crane et al.) discloses a method and apparatus for the colorimetric determination of the concentration of iron in process streams such as those encountered in the production of sodium hydroxide. The method is performed by withdrawing a sample from the process stream, adding color developing agents to the sample, transporting the sample plus developing agents to a transparent cell, and passing two light beams through the cell. One of the beams is of a color which is not absorbed by the sample and the other beam is of a color which is strongly absorbed by the sample. After passage through the sample, the beams are focused on separate photoelectric devices which are connected to a null balance circuit which measures the difference in output of the photoelectric cells as a function of the concentration of the color producing material (iron).

U.S. Pat. No. 2,737,591 (Wright et al.) discloses a method and apparatus for the analysis and control of organic systems in which a single beam of infrared light is passed through a sample cell containing a mixture to be analyzed. The beam is split by a beam splitter after passage through the sample, one split beam being directed to a light-responsive detector which is strongly absorptive of light of a distinctive wave length which is absorbed more strongly by the component to be determined in the analysis than by the other components of the mixture, and directing the second split beam to a light responsive deflector which does not strongly absorb light of the said distinctive wave length, but does absorb light of other wave lengths. Each detector develops an electric current or potential to an extent proportionate to the absorbed light energy, which can be monitored to indicate the concentration of the component to be determined.

U.S. Pat. No. 3,435,209 (Keahl) discloses a radiant energy analyzer by which radiation is directed alternately along first and second beam paths in each of which are located separate, independently operated wave length selectors such that radiant energy of differing wave lengths may be selected in each beam path. The beams are then recombined and focused onto a detector connected to an optical null servo loop. A sample cell can be placed in the beam path and certain optical characteristics of the sample can be measured.

U.S. Pat. No. 3,844,661 concerns an optical cell containing a fluid sample, the cell having a wiper blade mechanism to keep the cell clean, and selected wave lengths passed through the cell are measured by photosensor means.

U.S. Pat. No. 3,381,135 (Keller) discloses a double beam spectrophotometer utilizing an ultraviolet source of radiation of a relatively narrow band width of wave lengths to test the absorbance of a solution. The beam of light from the source is split into two beams, a reference sample of known concentration of material in a liquid is placed in the path of the first beam of light, and the second beam is caused to pass through a wedge of known concentration of material in a liquid which can be moved to cause the path length of light through the wedge to vary. The second beam of light also passes through a liquid of unknown concentration of material which is under test. The output from the spectrophotometer is used to control the absorbance of the liquid under test to maintain a predetermined necessary concentration of a material in the liquid under test.

U.S. Pat. No. 3,076,375 (Donnell) discloses a colorimeter having a linear absorbance scale. In this colorimeter, a beam of light is projected through a sample to be analyzed for color. The light transmitted through the sample is passed through a color filter which transmits substantially only the desired wave length, and then to a light detecting element or photocell. This cell is connected to an alternating current bridge circuit from which the output is fed to a logarithmic amplifier. The output of the amplifier is fed to a recorder having a linear scale, the reading of the scale being linearly related to the color concentration of the sample.

U.S. Pat. No. 3,652,861 (Engholdt) discloses a control device for detecting the hardness level of water. The device includes sampling means for extracting a sample of water from a water system and mixing the sample with a reagent which is formulated to cause the sample to change color at a predetermined hardness level. The mixed sample is exposed to a detection device which includes a bridge circuit and a voltage sensitive means connected to the bridge circuit for sensing an unbalanced condition in the bridge circuit. A pair of photoconductive cells are connected in series in one leg of the bridge circuit. One of the cells is positioned to receive light which has passed through the sample and the other cell is positioned to receive light which has passed through a filter element corresponding in color to a sample which is below a predetermined hardness level. When the hardness of the sample is below a preselected level, it will take on the color of the filter element and the light falling on both cells will be of substantially the same color and intensity. Thus, the bridge circuit will remain in a balanced condition. When the sample is above the preselected hardness level, it will assume a color different from that of the filter element. When this happens, the color and intensity of the light falling on the two cells will be different causing the bridge circuit to become unbalanced. The voltage sensitive means will sense this unbalanced condition and produce a signal which may be used to initiate the regeneration cycle of a water softener, for example.

U.S. Pat. No. 3,723,062 (Dahms) discloses a method and apparatus for colorimetric titration using an indicator which changes from one color to another at or near a titration endpoint, and an optical endpoint detection system which generates signals responsive to the relative concentration of the different colored forms of the indicator.

U.S. Pat. No. 3,308,712 (Kay) discloses a transducer for spectrum analysis including a polychromatic light source, a dynamic filter, and a detector. The dynamic filter allows light of one frequency to pass, the partcular frequency allowed to pass being variable as a function of time. When used as an absorption spectrometer, the light which passes through the dynamic filter is directed through a sample and then to a detector. The detector produces a signal which represents the absorption spectrum of the sample. When used to detect the emission spectra of the sample, the light source is replaced by the luminous sample and the light from the sample is directed through the dynamic filter to the detector.

None of the aforementioned references disclose the device and method of the invention herein which are described in detail and claimed hereinbelow.

SUMMARY OF THE INVENTION

According to this invention, a device and method are provided for measuring the concentration of a colored component contained in a flowing fluid in which a light source is used to direct light through a first frosted lens and then through a transparent sample cell containing inlet and outlet ports, then through a second frosted lens, and then a portion of the light is directed through a first filter and another portion of the light is directed through a second filter, these portions of light then being directed through a sight mask and onto a first and second photosensor such that substantially all light passing through the first filter is directed to the first photosensor and substantially all light passing through the second filter is directed to the second photosensor. The first filter is a filter which absorbs light which is absorbed by the colored component in the flowing stream, but which passes substantially all other light. The second filter is a filter which passes light absorbed by the colored component, but which absorbs substantially all other light. As the fluid containing the colored component to be monitored flows through the sample cell, the light energy reaching the photoconductors produces a potential difference in the output of the two sensors. The two photosensors are connected as resistance elements in a Wheatstone Bridge circuit, and the degree of upset of the null circuit, i.e. the difference in output potential between the photosensors is monitored. This difference is a function of the concentration of the colored component in the fluid, thereby enabling continuous monitoring of the concentration of this component. The potential difference between the outputs of the photosensors can be monitored continuously and displayed by any convenient means, and can be used to indicate an alarm when the potential difference (concentration) exceeds or falls below a predetermined value.

The method and apparatus of this invention are especially useful for monitoring the concentration of potassium permanganate in water systems.

BRIEF DESCRIPTION OF THE DRAWINGS

In the drawings.

FIGS. 3 and 4 show the light transmission characteristics of two light filters suitable for use according to this invention when potassium permanganate is the colored component in a liquid stream (water) desired to be monitored.

DETAILED DESCRIPTION OF THE INVENTION AND PREFERRED EMBODIMENTS

The method and apparatus of this invention can best be described in detail with reference to the drawings.

The color monitor of this invention, when used to measure the concentration of a colored component in a fluid stream, is especially suited for measuring extremely small concentrations. The monitor uses light filters having specific wave length absorption characteristics to detect the presence of or changes in concentration of the colored components of a level well below the level of human eye perception.

Figure 1:
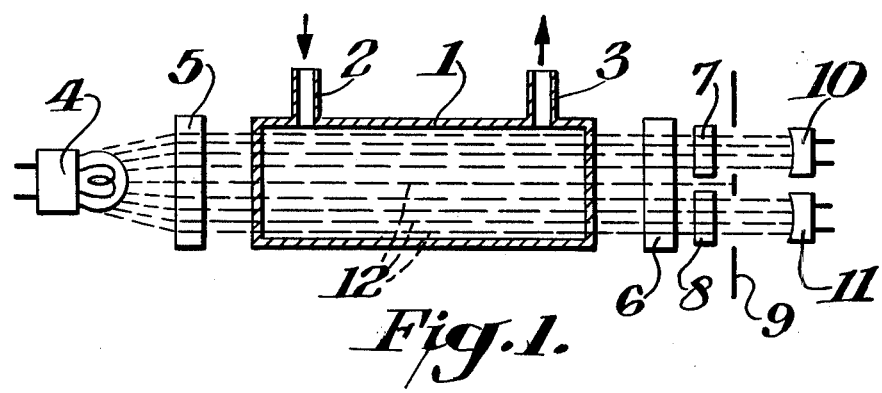
FIG. 1 shows the general arrangement of the light source, first lens, sample cell including inlet and outlet sample parts, second lens, selective filters, sight mask, and photosensors used in the invention.

In FIG. 1, the sample fluid containing the colored component to be monitored enters sample cell 1 through entry port 2 and exits the sample cell through exit port 3. In a preferred arrangement, the port 2 is located below sight tube 1 and sight tube 1 is inclined slightly from the horizontal to prevent entrapment and accumulation of air bubbles.

Light source 4 is located at one end of the transparent sample cell and light is directed into and through the sample cell through a first frosted lens 5. The light passing out of the sample cell is directed through second frosted lens 6, thence through selective wave length absorption filters 7 and 8, thence through sight mask 9 which divides the light in such a way that light passing through selective filter 7 impinges upon photosensor 10 and light passing through selective filter 8 impinges upon photosensor 11.

In FIG. 1, the light beams are shown as dashed lines 12.

Light source 4 is generally full spectrum polychromatic light. For certain specialized applications, other light sources may be used.

Lenses 5 and 6 are frosted lenses. These frosted lenses are especially useful in the method and apparatus of this invention since they effectively minimize variations in light intensity caused by impurities in the flowing stream. The diffuse light passing through the sample cell and eventually to the selective filters is substantially unaffected by relatively high levels of impurities. Compared to colorimetric devices which employ optical quality lenses wherein opaque impurities present cast a shadow causing a reduction in light intensity reaching the photosensors and resulting in an erroneous measurement, the diffuse light employed in the color monitor herein results in substantial insensitivity to such impurity particles. The diffuse light virtually bends around such particles and is collected at the second frosted lens 6 and directed to the selective filters. In a preferred embodiment, the frosted lenses are incorporated into the sight tube as the ends thereof, and the tube sealed with these lenses as endplates by means of gaskets.

The selective filters 7 and 8 are key elements of this invention. Selective filter 7 is chosen such that it has the same wave length absorption curve as the component to be detected; i.e. filter 7 absorbs light of the same wave length as the light absorbed by the component and passes substantially all other light of other wave lengths. Filter 8, on the other hand, is chosen such that it has wave length absorption characteristics which are just the inverse of those of filter 7, i.e. filter 8 is one which passes light of the same wave length as the light absorbed by the component to be detected and absorbs light of substantially all other wave lengths. Thus, small variations in sample opacity (due to impurities) or small variations in light intensity will have an equivalent effect on each photosensor and will not significantly affect the difference in the output of the two sensors, which difference is the variable directly relatable to concentration of the colored component in the system sought to be measured.

When small quantities of the component to be detected enter the sample cell, the component will absorb the light of wave lengths characteristic to that component. Because selective filter 7 is already absorbing those wave lengths (and passing all others), the light reaching photosensor 10 is substantially unchanged from that reaching this sensor when none of the colored component is present. However, the colored component absorbs the light characteristic to itself and thus decreases the amount of light reaching selective filter 8 (which passes light of wave lengths absorbed by the colored component) over that reaching filter 8 and photoconductor 11 when none of the desired component is present. Thus, a measurable difference in energy reaching the photosensors and in output of the sensors is established which is dependent upon the concentration of the colored component in the system, i.e. the higher the concentration of this component, the larger is the difference between the outputs of the two sensors.

The system may be easily calibrated using a fluid stream having various known concentrations of the colored component to be measured.

FIG. 3 shows the light transmission characteristics of a selective filter to be used as filter 8 when potassium permanganate is the component to be monitored. As can be seen in FIG. 3, this filter transmits light of wave length about 530 nanometers and absorbs most of the light of all other wave lengths. This filter is a green color compensating filter commercially available from Kodak under the product designation CC-40G.

FIG. 4 shows the light transmission characteristics of a selective filter to be used as filter 7 when potassium permanganate is the colored component desired to be monitored. This filter absorbs substantially all light at wave lengths of about 530 nanometers, which is the light absorbed by potassium permanganate. This filter is a magenta color compensating filter commercially available from the Kodak Company under product designation CC-40M.

Figure 2:
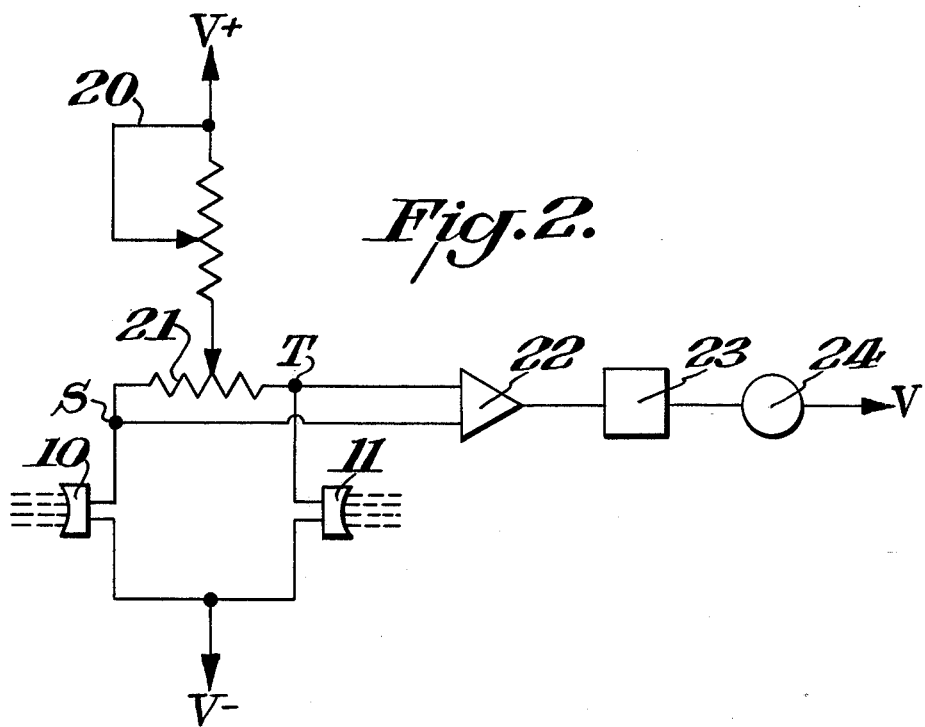
FIG. 2 is a diagram of the Wheatstone Bridge null circuit and associated electronic components used to sense the difference in voltage output from the photosensors and display or record this difference, or use this voltage difference to activate an alarm if the difference exceeds a predetermined level.

The photosensors 10 and 11 are connected as resistance elements in the Wheatstone Bridge null circuit shown in FIG. 2. When no colored component is present in the system, the bridge is balanced by applying voltages V+ and V− as shown and adjusting sensitivity adjustment 20 and calibration potentiometer 21. At null, there is little or no potential difference between points "S" and "T" shown in FIG. 2.

When the colored chemical being monitored enters the system, the voltage potential at point "T" will be higher than the potential at point "S". This difference in potential is sensed by voltage comparator 22 and the output from comparator 22 can be fed to relay driver 23 which supplies power to drive relay 24 activating an alarm, for example, if the potential difference exceeds (or drops below) a preset value. The relay driver is termed in the industry a "sink" driver. Voltage is applied to the driven device and the driver provides the return path. Components 23 and 23 are both connected to V+ and V− but these connections are not shown for clarity.

Alternatively, the potential difference may be conveniently displayed on a conventional meter or continuously recorded.

Example

The color monitor of this invention was used to continuously measure the concentration of potassium permanganate in a flowing water stream. The unit was capable of detecting a level of permanganate as low as 0.06 parts per million (PPM) in distilled water and as low as 0.25 PPM at a turbidity level of impurities (other than those having light absorbance similar to the colored component) corresponding to a 10% absorbance level.

In this unit an industry standard #57 light source powered by 12 VDC current was employed and the sample cell, containing inlet and outlet ports, was a 20 inch long sight tube. The frosted lenses were 3 inches in diameter and ⅜ inch thick (commercially available from the United Lens Co. as blanks under the product designation #8400231). The lenses were then ground and polished on one side and ground on the other.

The selective filters were those designated herein above (Kodak green and magneta color compensating filters) and were ¾ inch wide, ⅞ inch long and 0.004 inch thick (approximately).

The photosensors were commercially available sensors manufactured by the Clairex company under the product designation CL-905L.

In general, the instrument was capable of detecting permanganate in water having not over 10% total absorbance due to impurities having wave length absorbance characteristics different from the permanganate.

As the level of contaminants increased, the sensitivity of the instrument decreased. This decrease in sensitivity was not directly proportional to contaminant level, however. For example, the device was capable of detecting 0.25 PPM permanganate in water containing 1.0 PPM of iron.

The output from the two photosensors was fed to a voltage comparator, and a signal from the comparator was used to operate a relay, sounding an alarm when the permanganate level reached 0.25 PPM.

While the invention has been disclosed herein in connection with certain specific embodiments and details, it will be clear to one skilled in the art that changes or modifications may be made without deviating from the gist of the invention, and such changes or modifications are deemed to be within the scope of the claims appended below. In particular, reference has been made to potassium permanganate solutions herein. However, it is clear that this invention is useful for detecting any colored component in a fluid system through which light can be directed, within the scope of the tolerable impurity levels described above.

I claim:

1. A device for measuring the concentration of a colored component contained in a flowing fluid comprising:
   a. a light source;
   b. a first frosted lens;
   c. a transparent sample cell containing inlet and outlet ports;
   d. a second frosted lens;
   e. a first and second filter;
   f. a sight mask; and
   g. a first and second photosensor such that, as said fluid containing said colored component flows through said sample cell, light from said light source is directed through said first frosted lens, then through the sample cell, then through said second frosted lens, then a portion of the light is directed through said first filter and another portion of said light is directed through said second filter, then said portions of light are directed through said sight mask such that light passing through said first filter is directed to said first photosensor and light passing through said second filter is directed to said second photosensor, said first filter being a filter which absorbs light which is absorbed by the colored component being monitored and which passes substantially all other light, said second filter being one which passes light absorbed by said colored component and absorbs substantially all other light, and electronic means for measuring the difference in potential between the outputs of said first and second photosensors, which difference is generated by and is a function of the concentration of said colored component in said fluid.

2. A method for measuring the concentration of a colored component contained in a flowing fluid using the device of claim 1 comprising:
   directing light from the light source through the first frosted lens, thence
   through the transparent sample cell containing inlet and outlet ports through which said fluid flows, thence
   through the second frosted lens, a portion of the light passing through said second frosted lens being directed through the first filter and another portion of said light being directed through the second filter, thence
   said portions of light being directed through the sight mask such that light passing through the first filter is directed to the first photosensor and light passing through the second filter is directed to the second photosensor,
   the first filter being a filter which absorbs light which is absorbed by the colored component being monitored and which passes substantially all other light,
   the second filter being one which passes light absorbed by the colored component and absorbs substantially all other light
   and measuring the difference in potential between the outputs of the first and second photosensors, which difference is generated by and is a function of the concentration of the colored component in said fluid.

3. The method of claim 3 wherein the potential difference between the outputs of said photosensors is detected by use of a Wheatstone Bridge circuit.

4. The method of claim 2 including directing the outputs of said photoconductors by electronic means to an alarm system such that an alarm is indicated when the difference in potential between the output of the first photosensor and the output of the second photosensor exceeds a predetermined value.

* * * * *